United States Patent [19]

Thottathil

[11] Patent Number: 4,740,332

[45] Date of Patent: Apr. 26, 1988

[54] PROCESS FOR PREPARING PHOSPHONOUS ACIDS

[75] Inventor: John K. Thottathil, Lawrenceville, N.J.

[73] Assignee: E. R. Squibb & Sons, Inc., Princeton, N.J.

[21] Appl. No.: 4,513

[22] Filed: Jan. 20, 1987

Related U.S. Application Data

[63] Continuation-in-part of Ser. No. 861,794, May 12, 1986, abandoned.

[51] Int. Cl.$^4$ ............................................. C07F 9/48
[52] U.S. Cl. ..................... 260/502.4 R; 260/502.5 D; 560/130
[58] Field of Search ................. 260/502.4 R, 502.4 F, 260/502.4 E, 502.5 D; 560/130

[56] References Cited

U.S. PATENT DOCUMENTS

| | | | |
|---|---|---|---|
| 2,724,718 | 11/1955 | Stiles et al. | 260/502.4 |
| 2,957,931 | 10/1960 | Hamilton et al. | 260/502.4 |
| 3,812,222 | 5/1974 | Kleiner et al. | 260/502.4 |
| 4,108,889 | 8/1978 | Connor | 260/502.4 |
| 4,185,031 | 1/1980 | Gillman et al. | 260/502.4 |
| 4,374,780 | 2/1983 | Robertson | 260/502.4 |
| 4,452,790 | 6/1984 | Karanewsky et al. | 424/200 |
| 4,590,014 | 5/1986 | Wolf et al. | 260/502.4 |

OTHER PUBLICATIONS

Nifantey et al., "Synthesis of Alkyl-and Cycloalkyl-phosphonous Dichlorides and Their Conversion into Other Phosphonous Derivatives", J. Gen. Chem. (U.S.S.R.), 37 1293 (1967).

Morris et al., "Esters of Organophosphorus Acids", Chem. Abst. 10124b, 50 (1956).

Stiles et al., "Organophosphorus Compounds", Chem. Abst. 10124c, 50 (1956).

deBataafsche, "Production of Phosphonous Acid Derivatives", Chem. Abst. 8145c, 46 (1952).

Smith, "Intramolecular Esters of Hydroxy or Amino Phosphinic Acids", Chem. Abst. 8252d, 48 (1954).

Primary Examiner—J. E. Evans
Attorney, Agent, or Firm—Lawrence S. Levinson; Burton Rodney

[57] ABSTRACT

A process is provided for preparing phosphonous acids of the structure wherein $R_1$ is lower alkyl or arylalkyl

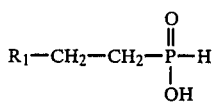

which are useful in preparing phosphinic and phosphonic acid ACE inhibitors, which process includes the steps of treating an olefin of the structure $R_1$—CH═$CH_2$ wherein $R_2$ is lower alkyl or arylalkyl with a phosphorus-containing reagent such as sodium hypophosphite or hypophosphorous acid in the presence of an organic alcohol solvent such as ethanol or methanol, and a radical initiator such as azobisisobutyronitrile, under acidic conditions, preferably at the reflux temperature of the organic solvent, to form the phosphonous acid without forming the alkyl ester.

13 Claims, No Drawings

PROCESS FOR PREPARING PHOSPHONOUS ACIDS

REFERENCE TO OTHER APPLICATIONS

This application is a continuation-in-part of U.S. application Ser. No. 861,794, filed May 12, 1986, now abandoned.

FIELD OF THE INVENTION

The present invention relates to a process for preparing phosphonous acids which are useful in preparing phosphonic acids and phosphinic acids which are used for preparing angiotensin converting enzyme inhibitors used in treating hypertension as disclosed in U.S. Pat. No. 4,452,790.

BACKGROUND OF THE INVENTION

Phosphonous acids are employing in preparing phosphonic acids and phosphinic acids and their derivatives thereof which are useful in preparing angiotensin converting enzyme inhibitors, as disclosed, for example, in U.S. Pat. No. 4,452,790 to Karanewsky, et al.

Until now, phosphonous acids have been prepared by high pressure reaction techniques wherein a high pressure bomb or autoclaves are employed as described by E. E. Nifantev and M. P. Koroteev, J. Gen. Chem. (U.S.S.R.), 37 1293 (1967); U.S. Pat. No. 2,726,256 to R. C. Morris and J. L. Van Winkle (assigned to Shell Development Co.), [C. A. 10124b, 50 (1956)]; N. V. de Bataafsche, Petroleum Maatschappig; British Pat. No. 660,918, Nov. 14, 1951, [C. A. 8145C, 46 (1952)]; U.S. Pat. No. 2,648,695 to C. W. Smith (assigned to Shell Development Co.), [C. A. 8252d, 48 (1954)].

In such prior art procedures, reactions were conducted in autoclaves (bombs) at high temperatures (120°–150° C.) and the products of the reaction presented a hard to separate mixture of alkylphosphonous and dialkylphosphinic acids with a total yield of 30–70%. The process of the present invention employs relatively mild conditions, namely, only refluxing in alcohol solvents in open vessel reactors to produce phosphonous acids in good yield and excellent purity.

U.S. Pat. No. 4,590,014 to Wolf et al discloses a method for preparing alkyl phosphinate salts by simultaneously adding an olefinic starting material (R—CH=CH$_2$) and a free radical initiator, such as benzoyl peroxide or azobisisobutyronitrile, to an aqueous alcoholic solution of sodium hypophosphite and allowing the reaction to continue for 1.5 to 6 hours. Due to the presence of the sodium salt starting material, the reaction medium must be maintained under neutral conditions to avoid converting the sodium salt to the hypophosphorous acid.

U.S. Pat. No. 2,957,931 to Hamilton et al discloses a process for preparing organic phosphorus compounds wherein at least one organic radical is joined to a phosphorus by a direct carbon-phosphorus linkage which process involves the reaction of phosphorus compounds having at least one phosphorus-hydrogen linkage per molecule (including hypophosphorous acid and sodium hypophosphite) with organic compounds having at least one unsaturated carbon-carbon linkage per molecule (which include 1-olefins), which reaction is carried out at temperatures of from 20° C. to 300° C. in the presence of water or alcohol solvent. As indicated in column 26, where water is used as a solvent, alkaline conditions would be preferred, where an alcohol solvent is employed, the alkyl ester is obtained.

U.S. Pat. No. 4,108,889 to Connor discloses a method for preparing alkane phosphonic acids by reacting an α-olefin with a macroreticular strong acid cation exchange resin to isomerize the olefin to form an internally unsaturated olefin, reacting such olefin with dimethyl phosphite in the presence of free radical initiator, such as di-t-butylperoxide, di-benzoylperoxide or azobisisobutyronitrile to produce non-terminally substituted C$_{12}$–C$_{22}$ alkanephosphonic acid dimethyl ester and demethylating the dimethyl ester with HCl or HBr.

U.S. Pat. No. 4,374,780 to Robertson discloses a method for preparing di-2,4,4'-trimethylpentylphosphinic acid by free radical addition of two moles of 2,4,4'-trimethylpentene-1 to phosphine employing high phosphine pressures of up to 100 psig, followed by oxidation with two moles of hydrogen peroxide. Azobisisobutyrylnitrile is employed as a free radical initiator.

DESCRIPTION OF THE INVENTION

In accordance with the present invention, a mild safe process is provided for preparing phosphonous acids, directly, without first preparing alkyl esters, wherein high pressures and unsafe gases such as phosphine are not required, which process may be described by the following reaction:

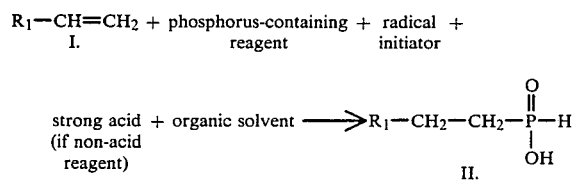

$$R_1-CH=CH_2 + \text{phosphorus-containing} + \text{radical} +$$
$$\text{I.} \qquad \text{reagent} \qquad \text{initiator}$$

$$\text{strong acid} + \text{organic solvent} \longrightarrow R_1-CH_2-CH_2-\overset{\overset{O}{\|}}{\underset{\underset{OH}{|}}{P}}-H$$
(if non-acid reagent)
$$\text{II.}$$

wherein R$_1$ is lower alkyl or arylalkyl.

In carrying out the above reaction, the olefin I is treated with a solution of phosphorus-containing reagent, namely, sodium hypophosphite or hypophosphorous acid, in an organic alcoholic solvent, which solution is cooled to a temperature of less than about 10° C., a radical initiator and strong acid (where sodium hypophosphite is employed as the phosphorus-containing reagent) under acidic conditions of pH of from about 0 to about 4 and preferably from about 0 to about 2. In this manner, the phosphonous acid product is prepared directly without first preparing an alkyl ester intermediate.

The above reaction is carried out at a temperature of within the range of from about 40° to about 120° C., preferably within the range of from about 50° to about 100° C., and optimally, at the refluxing temperature of the organic solvent, and for a period within the range of from about 2 to about 20 hours, and preferably for about 4 to about 12 hours.

In general, the phosphorus-containing reagent will be employed in a molar ratio to the olefin I of within the range of from about 0.5:1 to about 5:1 and preferably from about 1:1 to about 2:1.

The radical initiator will be usually employed in catalytic amounts but may be employed in a molar ratio to the olefin I of within the range of from about 0.01:1 to about 0.3:1. Examples of suitable radical initiators include, but are not limited to, azobisisobutyronitrile, di-t-butyl peroxide, benzoyl peroxide or hydrogen peroxide, with azobisisobutyronitrile being preferred.

Examples of alcohol solvents for the reaction include, but are not limited to, ethanol, methanol, isopropyl alcohol, t-butyl alcohol, with ethanol and methanol being preferred. Sufficient solvent will be employed to completely dissolve the reagents.

Where sodium hypophosphite ($NaH_2PO_2 \cdot H_2O$) is employed as the phosphorus-containing reagent, a strong acid such as $H_2SO_4$ or HCl, will be employed in the reaction mixture in order to maintain acidic conditions of pH of from about 0 to about 4 and preferably from about 0 to about 2. Such acid will normally be employed in a molar ratio to phosphorus-containing reagent of within the range of from about 0.5:1 to about 2:1, and preferably from about 1:1 to about 1.5:1.

The term "aryl," as used throughout the specification, either by itself or as part of a larger group, refers to phenyl or phenyl substituted with halogen, alkyl, alkoxy, alkylthio, hydroxy, alkanoyl, nitro, amino, dialkylamino, or trifluoromethyl groups. Phenyl and monosubstituted phenyl are preferred and phenyl is the most preferred.

The term "alkyl" or "lower alkyl," as used throughout the specification, either by itself or as part of a larger group, refers to straight or branched chain groups having 1 to 10 carbon atoms in the normal chain which may include an aryl, cycloalkyl or halo substituent, or amino substituent of the structure

where $R_2$ and $R_3$ may be the same or different and and can be H, lower alkyl, arylalkyl, aryl, t-butyloxycarbonyl, benzhydryl or trityl. Alkyl groups having 1 to 4 carbon atoms are preferred.

The term "cycloalkyl," as used throughout the specification, either by itself or as part of a larger group, refers to groups having 3 to 7 carbon atoms, such as cyclopropyl, cyclobutyl, cyclopentyl, cyclohexyl or cycloheptyl.

The term "arylalkyl" or "cycloalkylalkyl" as used through the specification, either by itself or as part of a larger group, refers to an "alkyl" group as defined above containing an "aryl" or "cycloalkyl" substituent.

The term "halo" or "halogen" as used throughout the specification, either by itself or as part of a larger group, refers to Cl, Br, F, I or $CF_3$.

Examples of olefins I useful as starting materials in carrying out the present invention include, but are not limited to, $C_2H_5-CH=CH_2$, $C_3H_7-CH=CH_2$, $C_6H_5(CH_2)_3-CH=CH_2$, $C_{10}H_{21}-CH=CH_2$, $C_6H_{13}CH=CH_2$, $C_4H_9CH=CH_2$, $C_5H_{11}CH=CH_2$, $C_6H_5CH_2-CH=CH_2$, $C_6H_5(CH)_2-CH=CH_2$,

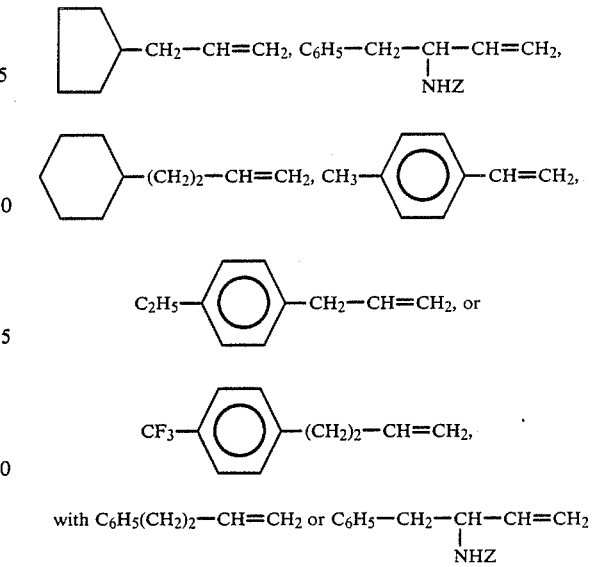

with $C_6H_5(CH_2)_2-CH=CH_2$ or $C_6H_5-CH_2-\underset{NHZ}{CH}-CH=CH_2$ being preferred.

The following examples are illustrative and represent preferred embodiments of the invention. Temperatures are given in degrees centigrade.

EXAMPLE 1

4-Phenylbutyl phosphonous acid (using azobisisobutyronitrile as the initiator catalyst)

A solution of sodium hypophosphite (2.41 g; 0.022727 moles; 3 equiv.) in ethanol (50 ml) was cooled below 0° C. in an ice/salt bath followed by the dropwise addition of concentrated $H_2SO_4$ (0.74 g; 0.007576 moles) (to provide a pH=~0.7). 4-Phenyl-1-butene (1.0 g; 0.007576 moles; 1 equiv.), and azobisisobutyronitrile (0.25 g; 0.001515 moles; 0.20 equiv.) were then added. The ice bath was removed and the mixture was heated to reflux temperature and stirred for 18 hours. The majority of the ethanol was removed on a rotavap at 40° C. and the residue was taken up in water (30 ml) and was basified with 10% aq. NaOH solution. The solution was extracted with ether (2×10 ml) followed by acidification of the aqueous layer with concentrated HCl. Solution was saturated with NaCl and extracted with ether (3×20 ml). Ether layers were combined and washed with deionized water (2×10 ml) and dried over $MgSO_4$. Solvent was removed on a rotavap to yield 1.14 g (76.0%) of title acid as a colorless oil, which solidified on standing at room temperature.

TLC, silica gel, 20:1:1 $CH_2Cl_2/CH_3OH/CH_3CO_2H$ showed single spot at $R_f=0.16$.

Anal Calc'd for $C_{10}H_{15}O_2P$: C, 60.61%; H, 7.58; P, 15.66%. Found: C, 60.59%; H, 7.69%; P, 15.6%.

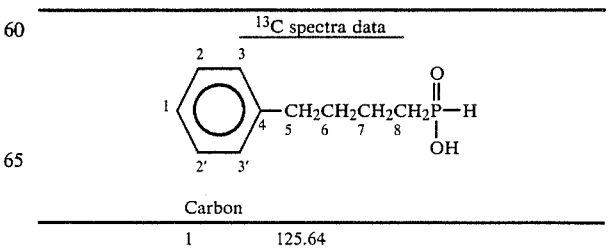

| Carbon | |
|---|---|
| 1 | 125.64 |

-continued

<sup>13</sup>C spectra data

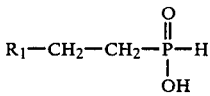

| Carbon | |
|---|---|
| 2, 3<br>2', 3' | 128.10 |
| 4 | 141.49 |
| 5 | 35.18 |
| 6 | 20.24 (2 Hz) |
| 7 | 31.80 (15.62 Hz) |
| 8 | 28.88 (93.75 Hz) |

EXAMPLE 2

4-Phenylbutylphosphonous acid (using hypophosphorous acid instead of sodium hypophosphite and sulphuric acid)

To a 50% water solution of hypophosphorous acid (2.41 gm, 0.023 moles) in ethanol (50 ml) (pH=~1.7) was added 4-phenyl-1-butene (1 gm, 0.0076 mole) and 0.1 gm of the radical initiator catalyst (azobiisobutyronitrile). The reaction mixture was refluxed for 20 hours and worked up as in Example 1, to produce the title compound in 80% yield (1.2 gm) as a colorless oil.

EXAMPLE 3

4-Phenylbutylphosphonous acid (using methanol as the solvent and sodium hypophosphite-sulfuric acid as the reagent)

To a solution of sodium hypophosphite (0.8 gm, 0.0076 mole) in methanol (25 ml) was added 4-phenyl-1-butene (0.5 gm, 0.0037 mole), radical initiator catalyst azobisisobutyronitrile (0.05 gm) and concentrated sulphuric acid (0.37 gm, 0.0037 moles) and the reaction mixture (having a pH=~1.8) refluxed for 20 hours with vigorous stirring. Usual workup as mentioned in Example 1 gave the title compound in 60% yield (0.45 gm) as colorless clear oil, which solidified on standing at ambient temperature.

EXAMPLE 4

4-Phenylbutylphosphonous acid (using methanol solvent and hypophosphorous acid as the solvent)

Following the procedure of Example 2 except using methanol as a solvent (pH=~1.6), instead of ethanol, the title product is obtained. Yield is 76%.

EXAMPLE 5

4-Phenylbutylphosphonous acid (using benzoyl peroxide as the catalyst)

The procedure used was similar to that described in Example 1, except benzoyl peroxide was substituted for azobisisobutyronitrile.

Thus, 0.5 gm of 4-phenyl-1-butene on reaction with 0.8 gm of sodium hypophosphite, and 0.37 gm of sulphuric acid and 0.04 gm of benzoyl peroxide in 25 ml ethanol produced 0.67 gm (89.3%) of the title product as a clear oil.

EXAMPLE 6 p-Fluorophenylbutyl phosphonous acid

The procedure as described in Example 1 was employed, except 4-(p-fluorophenyl)-1-butene was substituted for 4-phenyl-1-butene to produce the title compound as a colorless thick oil.

EXAMPLE 7 p-Trifluoromethylphenylbutyl phosphonous acid

The procedure as described in Example 2 was employed, except 4-(p-trifluoromethylphenyl)-1-butene was substituted for 4-phenyl-1-butene to produce the title compound as a thick oil.

EXAMPLE 8 n-Hexylphosphonous acid

The procedure as described in Example 1 is employed, except 1-hexene is substituted for 4-phenyl-1-butene to produce the title compound as a clear liquid.

EXAMPLE 9

3-Phenylpropyl phosphonous acid

A solution of hypophosphorous acid (2.41 g; 0.022727 moles; 3 equiv.) in ethanol (50 ml) was cooled below 0° C. in an ice/salt bath followed by dropwise addition of 3-phenyl-1-propene (1.0 g; 0.007576 moles; 1 equiv.), and 3-phenyl-1-propene azobisisobutyronitrile (0.25 g; 0.001515 moles; 0.20 equiv.). The ice bath was removed and the mixture was heated to reflux temperature and stirred for 18 hours. The majority of the ethanol was removed on a rotavap at 40° C. and the residue was taken up in water (30 ml) and basified with 10% aq. NaOH solution. The solution was extracted with ether (2×10 ml) followed by acidification of the aqueous layer with concentrated HCl. The solution was saturated with NaCl and extracted with ether (3×20 ml). Ether layers were combined and washed with deionized water (2×10 ml) and dried over MgSO₄. Solvent was removed on a rotavap to yield title acid as a colorless oil.

What is claimed is:

1. A process for preparing phosphonous acids of the structure

wherein R₁ is phenylalkyl, which comprises reacting an olefin of the structure

R₁—CH=CH₂ wherein R₁ is as defined above, with a phosphorus-containing reagent which is sodium hypophosphite or hypophosphorous acid, in the presence of an alcohol solvent which is ethanol or methanol and azobisisobutyronitrile as a radical initiator, at a temperature of within the range of from about 40° to about 120° C., under acidic conditions of pH of from about 0 to about 4, in an open vessel reactor, to form the phosphonous acid directly, without forming the alcohol ester, and recovering said phosphonous acid from the reaction mixture, wherein the phenyl is unsubstituted or substituted with halogen, alkyl, alkoxy, alkylthio, hydroxy, alkanoyl, nitro, amino, dialkylamino or $CF_3$.

2. The process as defined in claim 1 wherein the phosphorus-containing reagent is hypophosphorous acid.

3. The process as defined in claim 1 wherein the reaction is carried out at a pH of from about 0 to about 2.

4. The process as defined in claim 1 wherein the phosphorus-containing reagent is sodium hypophosphite and the olefin is treated with said sodium hypophosphite in the presence of a strong acid.

5. The process as defined in claim 4 wherein said strong acid is $H_2SO_4$ or HCl.

6. The process as defined in claim 1 wherein the radical initiator is employed in catalytic amounts.

7. The process as defined in claim 1 wherein the phosphorus-containing reagent is employed in a molar ratio to the olefin of within the range of from about 0.5:1 to about 6:1.

8. The process as defined in claim 1 wherein the radical initiator is employed in a molar ratio to the olefin of within the range of from about 0.01:1 to about 0.3:1.

9. The process as defined in claim 1 wherein the olefin is

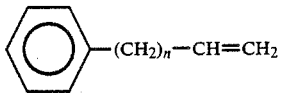

wherein n is 2, 3 or 4.

10. The process as defined in claim 1 wherein the reaction is carried out at a temperature of within the range of from about 50° to about 100° C.

11. The process as defined in claim 1 wherein the alcohol solvent is methanol.

12. The process as defined in claim 10 wherein the reaction is carried out at about the reflux temperature of the organic solvent.

13. The process as defined in claim 1 wherein the reaction is carried out for a period of from about 3 to about 20 hours.

* * * * *